(12) United States Patent
DeShazo et al.

(10) Patent No.: US 12,311,185 B2
(45) Date of Patent: *May 27, 2025

(54) IMPLANTABLE PULSE GENERATOR FOR PROVIDING A NEUROSTIMULATION THERAPY USING COMPLEX IMPEDANCE MEASUREMENTS AND METHODS OF OPERATION

(71) Applicant: ADVANCED NEUROMODULATION SYSTEMS, INC., Plano, TX (US)

(72) Inventors: Daran DeShazo, Lewisville, TX (US); Steven Boor, Plano, TX (US); Vidhi Desai, The Colony, TX (US)

(73) Assignee: ADVANCED NEUROMODULATION SYSTEMS, INC., Plano, TX (US)

( * ) Notice: Subject to any disclaimer, the term of this patent is extended or adjusted under 35 U.S.C. 154(b) by 781 days.

This patent is subject to a terminal disclaimer.

(21) Appl. No.: 17/447,272

(22) Filed: Sep. 9, 2021

(65) Prior Publication Data

US 2021/0402192 A1     Dec. 30, 2021

Related U.S. Application Data

(63) Continuation of application No. 16/370,357, filed on Mar. 29, 2019, now Pat. No. 11,135,439.

(51) Int. Cl.
*A61N 1/372* (2006.01)
*A61N 1/05* (2006.01)
*A61N 1/36* (2006.01)

(52) U.S. Cl.
CPC ....... *A61N 1/37252* (2013.01); *A61N 1/0534* (2013.01); *A61N 1/36067* (2013.01);
(Continued)

(58) Field of Classification Search
CPC .............. A61N 1/0534; A61N 1/36067; A61N 1/36071; A61N 1/3614; A61N 1/37229; A61N 1/37249; A61N 1/37252
See application file for complete search history.

(56) References Cited

U.S. PATENT DOCUMENTS

| 7,212,110 B1 | 5/2007 | Martin et al. |
| 8,594,785 B2 | 11/2013 | Bradley |

(Continued)

FOREIGN PATENT DOCUMENTS

| EP | 1784240 A | 5/2007 |
| WO | 2020197752 A1 | 10/2020 |

OTHER PUBLICATIONS

Authors et. al.: Disclosed Anonymously, "High-Speed Low-Power Voltage Comparator To Facilitate Automatic Compliance Voltage Control for a Neurostimulator", IP.com, IPCOM000016848D, Jul. 18, 2003, 13 pages.

(Continued)

*Primary Examiner* — Christopher A Flory
(74) *Attorney, Agent, or Firm* — Dean D. Small; The Small Patent Law Group, LLC

(57) ABSTRACT

Embodiments are directed to an implantable medical device comprising therapeutic stimulation circuitry for controlling delivery of a medical therapy to a patient, the therapeutic stimulation circuitry having at least one lead having electrodes for delivering the medical therapy, The implantable medical device further comprises measurement circuitry for determining characteristics of the at least one lead, a processor for controlling the IMD according to executable code, and memory for storing data and executable code, wherein the executable code comprises instructions for causing the processor to receive a plurality of voltage measurements (Continued)

associated with the electrodes, and calculate values for an impedance model of the electrode/tissue interface.

20 Claims, 11 Drawing Sheets

(52) U.S. Cl.
CPC ........ *A61N 1/36071* (2013.01); *A61N 1/3614* (2017.08); *A61N 1/37229* (2013.01); *A61N 1/37247* (2013.01)

(56) References Cited

U.S. PATENT DOCUMENTS

| | | | |
|---|---|---|---|
| 8,609,031 B2 | 12/2013 | Ohno et al. | |
| 9,054,436 B2 | 6/2015 | Swanson et al. | |
| 9,375,575 B2 | 6/2016 | Moffitt et al. | |
| 9,480,841 B2 | 11/2016 | Hershey et al. | |
| 9,656,084 B2 | 5/2017 | McDonald et al. | |
| 9,894,691 B1 | 2/2018 | Hellman et al. | |
| 10,258,799 B2 | 4/2019 | Steinke et al. | |
| 10,335,590 B2* | 7/2019 | Katnani | A61N 1/0534 |
| 10,960,211 B2 | 3/2021 | Hershey et al. | |
| 2005/0107841 A1 | 5/2005 | Meadows et al. | |
| 2006/0036186 A1* | 2/2006 | Goetz | A61N 1/37247 |
| | | | 600/547 |
| 2006/0173493 A1 | 8/2006 | Armstrong et al. | |
| 2006/0189854 A1 | 8/2006 | Webb et al. | |
| 2007/0066957 A1* | 3/2007 | Demarais | A61N 1/36007 |
| | | | 604/20 |
| 2007/0083239 A1* | 4/2007 | Demarais | A61N 1/327 |
| | | | 607/2 |
| 2007/0136098 A1 | 6/2007 | Smythe et al. | |
| 2008/0188909 A1* | 8/2008 | Bradley | A61N 1/36071 |
| | | | 607/59 |
| 2009/0024187 A1* | 1/2009 | Erickson | A61N 1/37247 |
| | | | 607/59 |
| 2009/0024189 A1* | 1/2009 | Lee | A61N 1/36017 |
| | | | 607/66 |
| 2009/0048643 A1* | 2/2009 | Erickson | A61N 1/378 |
| | | | 607/59 |
| 2009/0125081 A1 | 5/2009 | Spitzer et al. | |
| 2010/0023070 A1* | 1/2010 | Moffitt | A61N 1/36071 |
| | | | 607/2 |
| 2010/0125315 A1* | 5/2010 | Parramon | A61N 1/36157 |
| | | | 607/2 |
| 2012/0226200 A1* | 9/2012 | Wagner | A61N 1/36082 |
| | | | 607/45 |
| 2013/0150918 A1* | 6/2013 | Peterson | A61N 1/36146 |
| | | | 607/46 |
| 2014/0084949 A1* | 3/2014 | Smith | A61B 8/429 |
| | | | 324/693 |
| 2014/0277282 A1 | 9/2014 | Jaax | |
| 2014/0303691 A1* | 10/2014 | McDermott | A61N 1/36175 |
| | | | 607/72 |
| 2014/0343628 A1 | 11/2014 | Kaula et al. | |
| 2015/0005846 A1* | 1/2015 | Ranu | A61N 1/36521 |
| | | | 607/59 |
| 2015/0066108 A1* | 3/2015 | Shi | A61N 1/0534 |
| | | | 607/59 |
| 2015/0089590 A1 | 3/2015 | Krishnan et al. | |
| 2016/0045743 A1 | 2/2016 | Liu et al. | |
| 2016/0157769 A1* | 6/2016 | Min | G16H 20/40 |
| | | | 600/547 |
| 2016/0235984 A1 | 8/2016 | Karunasiri | |
| 2017/0001010 A1 | 1/2017 | Bradley et al. | |
| 2017/0209703 A1 | 7/2017 | Jiang et al. | |
| 2017/0259065 A1* | 9/2017 | Baru | A61N 1/36153 |
| 2017/0333720 A1* | 11/2017 | Astrom | A61N 1/36185 |
| 2018/0126172 A1* | 5/2018 | Sarkar | A61B 5/0537 |
| 2018/0243573 A1 | 8/2018 | Yoder et al. | |
| 2018/0345006 A1* | 12/2018 | Ambrose | A61B 5/0536 |
| 2019/0117964 A1* | 4/2019 | Bahrami | A61N 1/327 |
| 2020/0306533 A1 | 10/2020 | DeShazo et al. | |
| 2020/0306543 A1 | 10/2020 | Boor et al. | |
| 2020/0306550 A1 | 10/2020 | DeShazo et al. | |
| 2020/0309859 A1 | 10/2020 | DeShazo | |
| 2020/0353260 A1 | 11/2020 | Volkmann et al. | |

OTHER PUBLICATIONS

Authors et. al.: Disclosed Anonymously, "Circuitry for Using High-Speed Low-Power Voltage Comparator for Compliance Voltage Monitoring in Current-Mode Neurostimulator", IP.com, IPCOM000007552D, Apr. 4, 2002, 5 pages.
International Search Report, dated May 22, 2020, Application No. PCT/US20/021802, pp. 2.
Extended European Search Report for corresponding EP Application No. 19878741.8 dated Jun. 22, 2022 (8 pages).
Extended European Search Report for corresponding EP Application No. 20783790.7 dated Nov. 3, 2022 (11 pages).

* cited by examiner

IMPLANTABLE PULSE GENERATOR FOR PROVIDING A NEUROSTIMULATION THERAPY USING COMPLEX IMPEDANCE MEASUREMENTS AND METHODS OF OPERATION

RELATED APPLICATION

This application is a continuation of U.S. patent application Ser. No. 16/370,357, filed Mar. 29, 2019, which is incorporated herein by reference in its entirety.

BACKGROUND

Implantable medical devices have improved how medical care is provided to patients with certain types of chronic illnesses and disorders. For example, implantable cardiac devices improve cardiac function in patients with heart disease thereby raising quality of life and reducing morality rates. Implantable neurostimulator can provide pain reduction for chronic pain patients and reduce motor difficulties in patients with Parkinson's disease and other movement disorders. A variety of other medical devices are proposed and are in development to treat other disorders in a wide range of patients.

Neural activity in the brain can be influenced by electrical energy that Is supplied from a stimulation pulse generator or other waveform generator, Various patient perceptions and/or neural functions can be promoted or disrupted by applying an electrical or magnetic signal to the brain. Medical researchers and clinicians have attempted to manage various neurological conditions using electrical or magnetic stimulation signals to control or affect brain functions. For example, Deep Brain Stimulation (DBS) may reduce some of the symptoms associated with Parkinson's Disease, which results in movement or muscle control problems and Is debilitating to a great number of individuals worldwide.

A stimulation system pulse generator may be provided In various configurations, such as an implanted pulse generator (IPG). A typical IPG system configuration comprises of a surgically implanted, internally-powered pulse generator and multi-electrode lead. The implanted pulse generator may commonly be encased in a hermetically sealed housing and surgically implanted, for example, in a subclavicular, upper chest, or lower back location. An electrode assembly may be implanted to deliver stimulation signals to a stimulation site. The electrode assembly is coupled to the pulse generator via biocompatible and insulated lead wires. A power source, such as a battery, is contained within the housing of the pulse generator.

Brain anatomy typically requires precise targeting of tissue for stimulation by deep brain stimulation systems. For example, deep brain stimulation for Parkinson's disease commonly targets tissue within or dose to the subthalamic nucleus (STN). The STN is a relatively small structure with diverse functions. Stimulation of undesired portions of the STN or immediately surrounding tissue can result in undesired side effects. For example, muscle contraction or muscle tightening may be caused by stimulation of neural tissue that is near the STN. Mood and behavior dysregulation and other psychiatric effects have been reported from undesired stimulation of neural tissue near the STN in Parkinson's patients.

To avoid undesired side effects in deep brain stimulation, neurologists often attempt to identify a particular electrode for stimulation that only stimulates the neural tissue associated with the symptoms of the underlying disorder while minimizing use of electrodes that stimulate other tissue. Also, neurologists may attempt to control the pulse amplitude, pulse width, and pulse frequency to limit the stimulation field to the desired tissue.

As an improvement over conventional deep brain stimulation leads, leads with segmented electrodes have been proposed. Conventional deep brain stimulation leads include electrodes that fully circumscribe the lead body. Leads with segmented electrodes include electrodes on the lead body that only span a limited angular range of the lead body. As used herein, the term "segmented electrode" refers to an electrode or a group of electrodes that are positioned at approximately the same longitudinal location along the longitudinal axis of a lead and that are angularly positioned about the longitudinal axis so they do not overlap and are electrically isolated from one another. For example, at a given position longitudinally along the lead body, three electrodes can be provided with each electrode covering respective segments of less than 120 degrees about the outer diameter of the lead body. By selecting between such electrodes, the electrical field generated by stimulation pulses or waveforms can be more precisely controlled and, hence, stimulation of undesired tissue—which often causes detrimental therapy side effects—can be more easily avoided. This has particular benefit for improved stimulation therapy efficacy if the DBS lead is slightly misplaced from the target area in the brain during surgical implantation.

Implanted medical devices may estimate the impedance of the patient load by taking a voltage or current measurement during a sub-perception stimulation pulse or at the end of a therapy stimulation pulse, If the implanted medical device delivers a controlled voltage, then a current measurement can be used to estimate impedance. If the device delivers a controlled current, then a voltage measurement can be used to estimate impedance. In either of these cases, a single measurement provides only an estimation of a resistance since there is no time-dependent Information in the measurement External test equipment, such as a Potentiostat is often used in research to allow characterization via electrochemical impedance spectroscopy and analysis of the electrode/tissue interface for modelling purposes. However, such measurement is typically limited to animal (e.g., non-human primates, ovine, and rodent) studies, and the results provide only a theoretical basis for clinically relevant models that may not be accurate for a specific patient using a specific electrode lead and their particular stimulation control parameters with their implanted medical device.

SUMMARY

Figure 1:
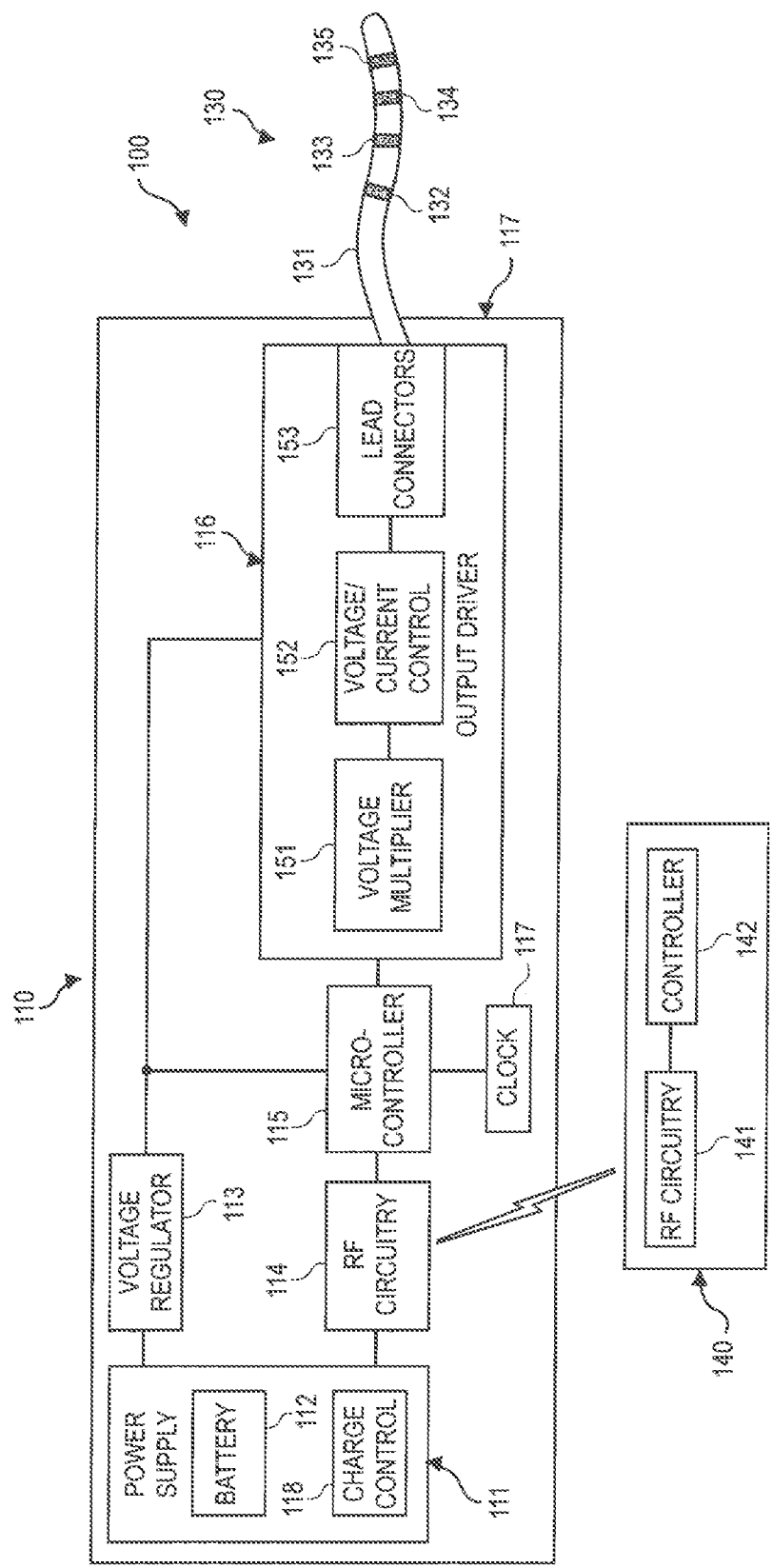
FIG. 1 depicts a neurostimulation system that is adapted according to an example embodiment and is shown as a high-level functional block diagram.

In an example embodiment, an implantable medical device comprises therapeutic circuitry for controlling delivery of a medical therapy to a patient, the therapeutic circuitry having at least one lead having electrodes for delivering the medical therapy. The implantable medical device further comprises measurement circuitry for determining characteristics of the at least one lead, a processor for controlling the IMD according to executable code, and memory for storing data and executable code, wherein the executable code comprises instructions for causing the processor to (1) receive a plurality of voltage measurements associated with the electrodes, and (2) calculate component values for an impedance model of the electrodes.

In an embodiment, the executable code further comprises Instructions for causing the processor to (3) adjust a medical therapy for the patient based upon the values for the impedance model for a selected set of electrodes.

In an embodiment, the executable code further comprises instructions for causing the processor to (3) save a first set of values for the impedance model for a set of electrodes, (4) save a second set of values for the Impedance model for the set of electrodes, and (5) identify a difference between the first set of values and the second set of values. The difference may correspond, for example, to a change in state for the set of electrodes and/or a change in the position or health of the patient.

In an embodiment, the impedance model comprises capacitances associated with an electrode/tissue interface and a resistance associated with tissue between electrodes. The capacitances associated with the electrode/tissue interlace correspond to a rate of change of voltage measurements captured during a therapy pulse. The resistance associated with tissue between electrodes corresponds to a voltage measurement captured at the beginning of a therapy pulse. The impedance model may further comprise Faradaic resistances associated with the electrode/tissue interface.

In an embodiment, the measurement circuitry comprises a multiplexer coupled to a plurality of electrodes, a differential buffer coupled to the multiplexer, a filter for properly capturing therapeutic stimulation waveforms from the buffer, and a differential analog-to-digital converter coupled to the filter for generating a digital output corresponding to the voltage measurements.

In an embodiment, a method of monitoring electrodes in an implantable medical device comprises delivering stimulation therapy comprising a plurality of electrical waveforms applied to a patient via electrodes coupled to the patient's tissue, receiving a first set of voltage measurements associated with the electrodes, and calculating a first set of values for an impedance model of the electrodes using the first set of voltage measurements.

The method may further comprise adjusting stimulation therapy for the patient based upon the values for the impedance model for a selected set of electrodes.

The method may further comprise receiving a second set of voltage measurements associated with the electrodes, calculating a second set of values for an impedance model of the electrodes using the second set of voltage measurements, and determining a difference between the first set of values and the second set of values, in an embodiment, the difference may correspond to a change in status for a set of electrodes. In another embodiment, the difference may correspond to a change in the health or position of the patient.

In an example embodiment, the impedance model used in the method comprises capacitances associated with an electrode/tissue interface and a resistance associated with tissue between electrodes, the capacitances associated with the electrode tissue interface correspond to a rate of change of voltage measurements captured during therapy. The resistance associated with tissue between electrodes corresponds to a voltage measurement captured at the beginning of a therapy pulse. The impedance model used in the method may further comprise Faradaic resistances associated with the electrode/tissue Interface.

In an embodiment, receiving the first set of voltage measurements in the method further comprises receiving inputs form a plurality of electrodes at a multiplexer, providing inputs from selected sets of electrodes from the multiplexer to a differential buffer, filtering the inputs from selected sets of electrodes to properly capture therapeutic stimulation waveforms, and generating a digital output from a differential analog-to-digital converter using the filtered inputs, the digital output corresponding to the voltage measurements.

DETAILED DESCRIPTION

FIG. 1 depicts a neurostimulation system 100 that is adapted according to an example embodiment and is shown as a high-level functional block diagram. Neurostimulation systems are devices that generate electrical pulses and deliver the pulses to neural tissue of a patient to treat a variety of disorders. As noted above, a neurostimulation system 100 may be used to provide DBS therapy for patients with movement disorders. Neurostimulation system 100 may also provide Spinal Cord Stimulation (SCS) in which electrical pulses are delivered to neural tissue of the spinal cord for the purpose of chronic pain control While a precise understanding of the interaction between the applied electrical energy and the neural tissue is not fully appreciated, it is known that application of an electrical field to spinal neural tissue can effectively inhibit certain types of pain transmitted from regions of the body associated with the stimulated neural tissue to the brain.

Neurostimulation systems generally include a pulse generator and one or more leads. A stimulation lead includes a lead body of insulative material that encloses wire conductors. The distal end of the stimulation lead includes multiple electrodes that are electrically coupled to the wire conductors. The proximal end of the lead body includes multiple terminals (also electrically coupled to the wire conductors) that are adapted to receive electrical pulses. For SCS therapy, the distal end of a respective stimulation lead is implanted within the epidural space to deliver the electrical pulses to the appropriate nerve tissue within the spinal cord. The stimulation leads are then tunneled to another location within the patient's body to be electrically connected with a pulse generator or, alternatively, to an "extension."

The pulse generator is typically implanted within a subcutaneous pocket created during the implantation procedure. In SCS, the subcutaneous pocket is typically disposed in a lower back region, although subclavicular implantations and lower abdominal implantations are commonly employed for other types of neuromodulation therapies.

Neurostimulation system 100 of the illustrated embodiment includes a generator portion, shown as implantable pulse generator (IPG) 110, for providing a stimulation or energy source, a stimulation portion, shown as lead 130, for application of the stimulus pulse(s), and an optional external controller, shown as programmer/controller 140, to program and/or control IPG 110 via a wireless communications link. IPG 110 may be implanted within a living body (not shown) for providing electrical stimulation from IPG 110 to a selected area of the body, such as a region of the brain or spinal cord, via lead 130. In some embodiments, IPG 110 provides electrical stimulation under control of external programmer/controller 140. It should be appreciated that, although lead 130 is illustrated to provide a stimulation portion of stimulation system 100 and is configured to provide stimulation remotely with respect to the generator portion 110 of stimulation system 100, a lead 130 as described herein is intended to encompass a variety of stimulation portion configurations. Furthermore, a lead configuration may include more (e.g., 8, 16, 32, etc.) or fewer (e.g., 1, 2, etc.) electrodes than those represented in the illustrations.

IPG 110 of the illustrated embodiment includes power supply 111, voltage regulator 113, RF circuitry 114, microcontroller (or microprocessor) 115, output driver circuitry 116, and clock 117, as are described in further detail below. Power supply 111 provides a source of power, such as from battery 112, to other components of IPG 110, as may be regulated by voltage regulator 113. Battery 112 may comprise a non-rechargeable (e.g., single use) battery, a rechargeable battery, a capacitor, and/or like power sources, Charge control 118 provides management for battery 112 and power supply 111 in some embodiments. In some embodiments, the entire IPG 110 device may need to be accessed by a surgical procedure to replace battery 112. In other embodiments, when battery 112 is depleted, it may be recharged after being implanted, for example, inductive coupling and external charging circuits. Circuitry for recharging a rechargeable battery of an implantable pulse generator using inductive coupling and external charging circuits are described in U.S. Pat. No. 7,212,110, entitled "IMPLANTABLE DEVICE AND SYSTEM FOR WIRELESS COMMUNICATION," which is incorporated herein by reference.

RF circuitry 114 provides data communication between microcontroller 115 and controller 142 in external programmer/controller 140, via RF circuitry 141. It should be appreciated that RF circuitry 114 and/or 141 may be a receiver, a transmitter, and/or transceiver depending upon the communication links desired using far-field and/or near field communication communications. The communication links may be established using suitable communication methods such as inductive wireless communication, low energy BLUETOOTH® communication, and medical band wireless communication as examples. An example of BLU- ETOOTH@ communication between an implantable medical device and a programmer device is found, for example, in U.S. Pat. No. 9,894,691, entitled SYSTEMS AND METHODS FOR ESTABLISHING A COMMUNICATION LINK BETWEEN AN IMPLANTABLE MEDICAL DEVICE AND AN EXTERNAL INSTRUMENT, the disclosure of which is incorporated herein by reference.

Microcontroller 115 provides control with respect to the operation of IPG 110, such as in accordance with a program provided thereto by external programmer/controller 140. Software code is typically stored in memory (not shown) of IPG 110 for execution by the microcontroller 115 to control the various components of the device. The software code stored in memory of IPG 110 may support operations of embodiments disclosed herein.

Output driver circuitry 116 generates and delivers pulses to selected ones of electrodes 132-135 on lead body 131 under control of microcontroller 115. For example, voltage multiplier 151 and voltage/current control 152 may be controlled to deliver a constant current pulse of a desired magnitude using selected ones of electrodes 132-135. Clock 117 preferably provides system timing information, such as may be used by microcontroller 115 in controlling system operation, as may be used by voltage multiplier 151 in generating a desired voltage, etcetera.

Lead 130 of the illustrated embodiment includes lead body 131, preferably incorporating a plurality of internal conductors coupled to lead connectors (not shown) to interface with lead connectors 153 of IPG 110. Lead 130 further includes electrodes 132-135, which are preferably coupled to the internal conductors 153. The internal conductors provide electrical connection from individual lead connectors to each of a corresponding one of electrodes 132-235. In the exemplary embodiment the lead 130 is generally configured to transmit one or more electrical signals from IPG 110 for application at, or proximate to, a spinal nerve or peripheral nerve, brain matter, muscle, or other tissue via electrodes 132-135. IPG 110 is capable of controlling the electrical signals by varying signal parameters, such as pulse amplitude, pulse width, pulse frequency, burst frequency, and/or the like in order to deliver a desired therapy or otherwise provide operation as described herein.

Although the embodiment illustrated in FIG. 1 includes four electrodes, it should be appreciated that any number of electrodes, and corresponding conductors, may be utilized according to some embodiments. Moreover, various types, configurations and shapes of electrodes (and lead connectors) may be used according to some embodiments. An optional lumen (not shown) may extend through the lead 130, such as for use in delivery of chemicals or drugs or to accept a stylet during placement of the lead within the body. Additionally, or alternatively, the lead 130 (stimulation portion) and IPG 110 (generator portion) of stimulation system 100 may comprise a unitary construction, such as that of a microstimulator configuration.

In an embodiment, a programmable neurostimulation system 100 supplies suitable therapy pulses to a patient by enabling a pattern of electrical pulses to be varied across the electrodes 132-135 of a lead or leads 130. Such systems enable electrodes of a connected stimulation lead 130 to be set as an anode(+), as a cathode(−), or to a high-impedance state (OFF). As is well known, negatively charged ions flow away from a cathode toward an anode. Consequently, a range of very simple to very complex electrical fields can be created by defining different electrodes 132-135 in various combinations of (+), (−), and OFF. Of course, in any instance, a functional combination must include at least one anode and at least one cathode. In an embodiment, the case or "can" of the neurostimulation system 100 or IPG 110 may function as an anode. When determining the appropriate electrode configurations, the selection of electrodes 132-135 to function as anodes can often facilitate isolation of the applied electrical field to desired fibers and other neural structures. Specifically, the selection of an electrode 132-135 to function as an anode at a position adjacent to another electrode functioning as a cathode causes the resulting electron/ion flow to be limited to tissues immediately surrounding the two electrodes. By alternating through the possible anode/cathode combinations, it is possible to gain greater resolution in the stimulation of desired tissue or neural structures.

As mentioned above, programmer/controller 140 provides data communication with IPG 110, such as to provide control (e.g., adjust stimulation settings), provide programming (e.g., alter the electrodes to which stimulation pulses are delivered), etc. Accordingly, programmer/controller 140 of the illustrated embodiment includes RF circuitry 141 for establishing a wireless link with IPG 110, and controller 142 to provide control with respect to IPG 110. Programmer/controller 140 may receive data from IPG 110 that can be displayed to medical personnel or a clinician on a screen (not shown) on programmer/controller 140. Additionally, or alternatively, programmer/controller 140 may provide power to IPG 110, such as via RF transmission by RF circuitry 141. Optionally, however, a separate power controller may be provided for charging the power source 111 within IPG 110.

Additional detail with respect to pulse generation systems and the delivery of stimulation pulses may be found in U.S. Pat. No. 6,609,031, entitled "MULTIPROGRAMMABLE TISSUE STIMULATOR AND METHOD," the disclosure of which is hereby incorporated herein by reference. Similarly, additional detail with respect to pulse generation systems and the delivery of stimulation pulses may be found in U.S. Pat. No. 7,937,158, entitled "MULTIPROGRAMMABLE TRIAL STIMULATOR."

Having generally described stimulation system 100 above, the discussion which follows provides detail with respect to various functional aspects of stimulation system 100 according to some embodiments. Although the below embodiments are described with reference to stimulation system 100, and IPG 110 thereof, it should be appreciated that the inventive concepts described herein are not limited to application to the exemplary system and may be used in a wide variety of medical devices.

Figure 2:
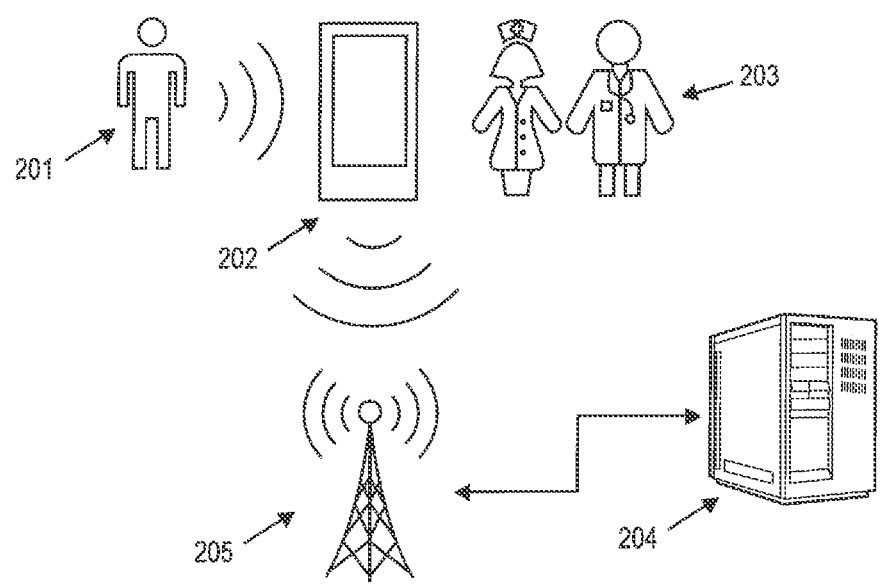
FIG. 2 depicts a system in which an implanted medical device may be programmed and/or monitored by a programmer device to provide therapy according to some representative embodiments.

FIG. 2 depicts a system in which an implanted medical device may be programmed and/or monitored by a programmer device to provide SCS or DBS according to some representative embodiments. The implanted medical device (not shown in FIG. 2) is implanted within patient 201. Examples of suitable implantable medical devices include neurostimulators such as the Protege™, Prodigy™, Proclaim™, Infinity™ pulse generators available from Abbott (Plano, TX).

At appropriate times, the implanted medical device of patient 201 communicates with clinician programmer device 202, which is operated by one or more clinicians 203. The programming clinician 203 utilizes one or more user interface screens of device 202 to define or control a therapy provided to patient 201 by the implanted medical device, The clinician(s) may define or set one or more therapy parameters. For example, the clinician may define pulse amplitudes, pulse frequencies, pulse patterns, and/or a variety of other therapy parameters depending upon the implanted device and the intended therapy for patient 201.

During a programming session, programming data may be communicated from clinician programmer device 202 to one or more remote device management servers 204 via network 205. The set of programming data is subjected to authorization and validation processes to ensure that only programming data from authorized clinicians will be accepted by the implanted medical device of patient 201. Suitable security algorithms may be employed to validate and authorize communication between clinician programmer device 202 and servers 204, such as communication of user/clinician identifiers, passwords, device identifiers, network identifiers, security/cryptographic keys, digital certificates, location data, and/or the like. The implanted medical device of patient 201 may also provide information, such as battery life data, to clinician programmer device 202. In an embodiment, when the patient 201 is about to undergo an MRI scan or is being exposed to EMI, the programming clinician 203 may use programmer device 202 to communicate with the implanted medical device of patient 201 and direct the implanted medical device to enter an active discharge mode. The active discharge mode may be programmed by clinician programmer device 202 to last for a predetermined duration or until instructed to enter a passive discharge mode.

As noted above, it is well known in the implantable device industry that passive discharge after stimulation has been proven clinically advantageous for minimizing undesirable side effects from the stimulation therapy. A stimulation pulse is delivered to target neurons, such as in the brain, spinal cord, or nervous system in general, through electrodes 132-135 on lead body 131 as shown in FIG. 1. Each stimulation pulse causes charge to build up on capacitors in that stimulation loop. This charge must be eliminated. Otherwise, the charge will continue to build up and eventually prevent the system from delivering therapy pulses to the patient. Charge that builds up over time can also lead to chemical reactions in the patient's body that are bad for the electrodes and for the patient. Normally, the IPG Is designed to dissipate the charge using passive discharge that builds up within the stimulation loop by shorting the stimulation electrodes together after delivering a stimulation pulse. By shorting the electrodes together, charge on the stimulation loop is dissipated. Using this shorting mechanism is free in terms of power cost as it does not require anything from the battery.

However, when the electrodes are shorted together, this creates a low impedance electrical loop that can interact with an MRI scan and cause currents to flow through the loop, which can stimulate the patient unexpectedly. This can cause discomfort in the patient, which can be very dangerous. Moreover, any MRI-induced currents may damage or change the characteristics of the stimulation lead itself. As a result, great care must be exercised with the IPG when using the passive discharge method during an MRI scan; passive discharge is universally avoided with DBS therapy using a Monopolar stimulation configuration, which is the most commonly used and most efficient method of delivering DBS therapy to patients.

Embodiments disclosed herein describe a means for emulating passive discharge of stimulation electrodes with a programmable amplitude IPG current regulator that creates an active discharge. This maintains a high impedance stimulation loop and allows the IPG to circumvent the therapy degradation risks and safety concerns raised by using passive discharge of electrodes during an MRI scan and other types of EMI, especially with Monopolar DBS therapy when the IPG Can is used as a stimulation electrode. The emulated passive discharge embodiment has the same benefit as passive discharge in minimizing undesirable therapeutic side effects as well as reducing the time and effort needed for IPG device programming to achieve therapy efficacy in the presence of MRI and EMI. Passive discharge simply requires dosing a switch to short the electrodes, which does not draw any current from the battery. Due to the minimal power requirements, passive discharge is a preferred method. However, as noted above, passive discharge has potentially detrimental side effects during an MRI especially when a Monopolar stimulation configuration is utilized. To address this problem, embodiments described herein use active discharge to dissipate the charge that builds up within the stimulation loop. Active discharge can be used to emulate passive discharge using the same type of circuit and current stimulus delivery system as used to deliver the stimulation pulse. In active discharge, the electrodes are essentially reversed, and current flows in the opposite direction relative to how it flows during the therapy pulse (i.e., a reverse pulse). This has the same charge dissipation effect as closing a switch to short the electrode leads In passive discharge. Accordingly, active discharge uses the same stimulation method as therapy delivery.

Because active discharge requires an active circuit that draws current from the battery, it is not preferred for full-time use. Instead, in an embodiment, an IPG can be directed to perform active discharge during an MRI or when exposed to other forms of EMI. Since patients are not in an MRI often or for long periods of time, the active discharge method is typically required only for a short period of time. Active discharge allows the IPG to continue providing therapy to the patient even while undergoing an MRI or when exposed to EMI The cost for intermittent use of active discharge is some minimal additional battery current to keep the therapy going while exposed to the MRI or EMI.

Existing IPG devices do not use active discharge for DBS therapy due to concerns that active discharge pulses may inadvertently recruit neurons in the non-target areas exposed to the reverse pulse. Embodiments address this concern by allowing the current to exponentially decay instead of outputting a constant current from the active discharge circuitry. The active discharge with exponential decay behaves the same as passive discharge for patients therapeutically and in dissipating built-up charge after stimulation, but the active discharge is much less susceptible to stimulation interference in an MRI or EMI field because it exhibits a high output impedance to the discharge path. This eliminates the limitations of existing passive discharge schemes and allows the IPG to provide the same therapy while overcoming MRI degradation.

Figure 3:
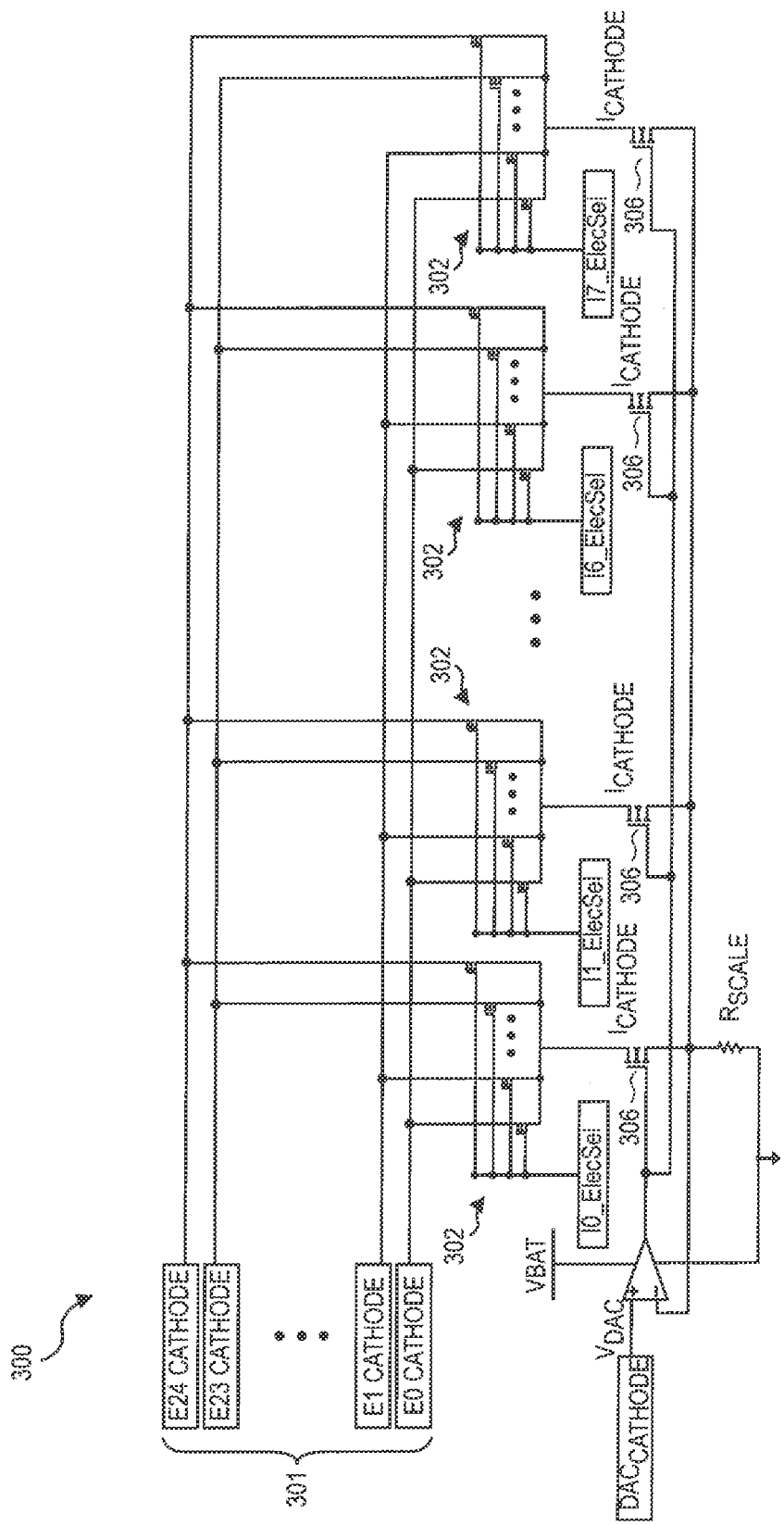
FIG. 3 depicts a cathode-side programmable amplitude current regulator according to one embodiment for providing active discharge pulses.

FIG. 3 depicts a cathode-side programmable amplitude current regulator 300 according to one embodiment for providing active discharge pulsesin an IPG. The programmable amplitude current regulator 300 comprises a plurality of cathode electrodes 301 that may be programmed as the cathode from the patient. An IPG delivers stimulation in an embodiment by generating an anode voltage with a voltage multiplier (not shown). The anode voltage is connected to an anode electrode that is implanted in the patient. The IPG also programs one or more cathode electrodes 301 that pull the current from the anode electrode The voltage originates from the voltage multiplier, flows out of the anode electrode, through the patient to the cathode electrode, and then back through the cathode electrode through current regulator 300. Electrode selection circuits 302 are used to select which cathode electrode 301 is active. In an embodiment, electrode selection circuits 302 use field-effect transistor (FET) transistors for electrode connectivity to the current regulator.

Digital to analog converter (DAC) cathode 303 is a digitally-controlled voltage source that provides a reference voltage. DAC cathode 303 provides an input voltage ($V_{DAC}$) to an error amplifier 304, The voltage for the other input to error amplifier 304 is set by programmable resistor ($R_{SCALE}$) 305, which may be, for example, a resistance network that is programmed digitally. The stimulation therapy current ($I_{CATHODE}$) that is provided to the patient is determined by Ohm's law: $I = V_{DAC}/R_{SCALE}$. This current is programmed to last for a certain duration that is referred to herein as pulse width. The cathode current isoutput for a limited duration and is then shut off, which essentially provides a constant current pulse for a given amount of pulse width. Cathode-side programmable amplitude current regulator 300 changes how discharge current Is delivered compared to existing IPGs. Instead of keeping the voltage through DAC 303 at a constant value, which is what normally occurs for an active discharge pulse, the current regulator 300 digitally changes the code in DAC 303 so that the output $V_{DAC}$ changes with time like an exponentially decaying circuit This has the effect of mimicking passive discharge, which conducts an exponentially decreasing current over time, by changing the digital voltage reference going into error amplifier 304.

In an embodiment such as IPG 110 (FIG. 1), electrode selection circuits 302 and connections to cathode electrodes 301 may be components of lead connectors 153 and current generator elements (DAC 303, error amplifier 304, and variable resistor 305) may be components of voltage/current control 152. Electrodes 132-135 on lead body 131 may function as anodes or cathodes.

The exponentially-decreasing discharge current amplitude can be digitally programmed via the DAC cathode 303 input for the current regulator 300 to emulate a passive discharge. In an embodiment, a pre-calculated sequence of current pulses may be provided in a table. In some embodiments, the pre-calculated sequence is determined by measuring complex impedance values for electrodes to be used for stimulation of patient neural tissue and forming the discharge current based on the measured values. In some embodiments, the measurements are conducted using methods discussed herein.

Figure 4:
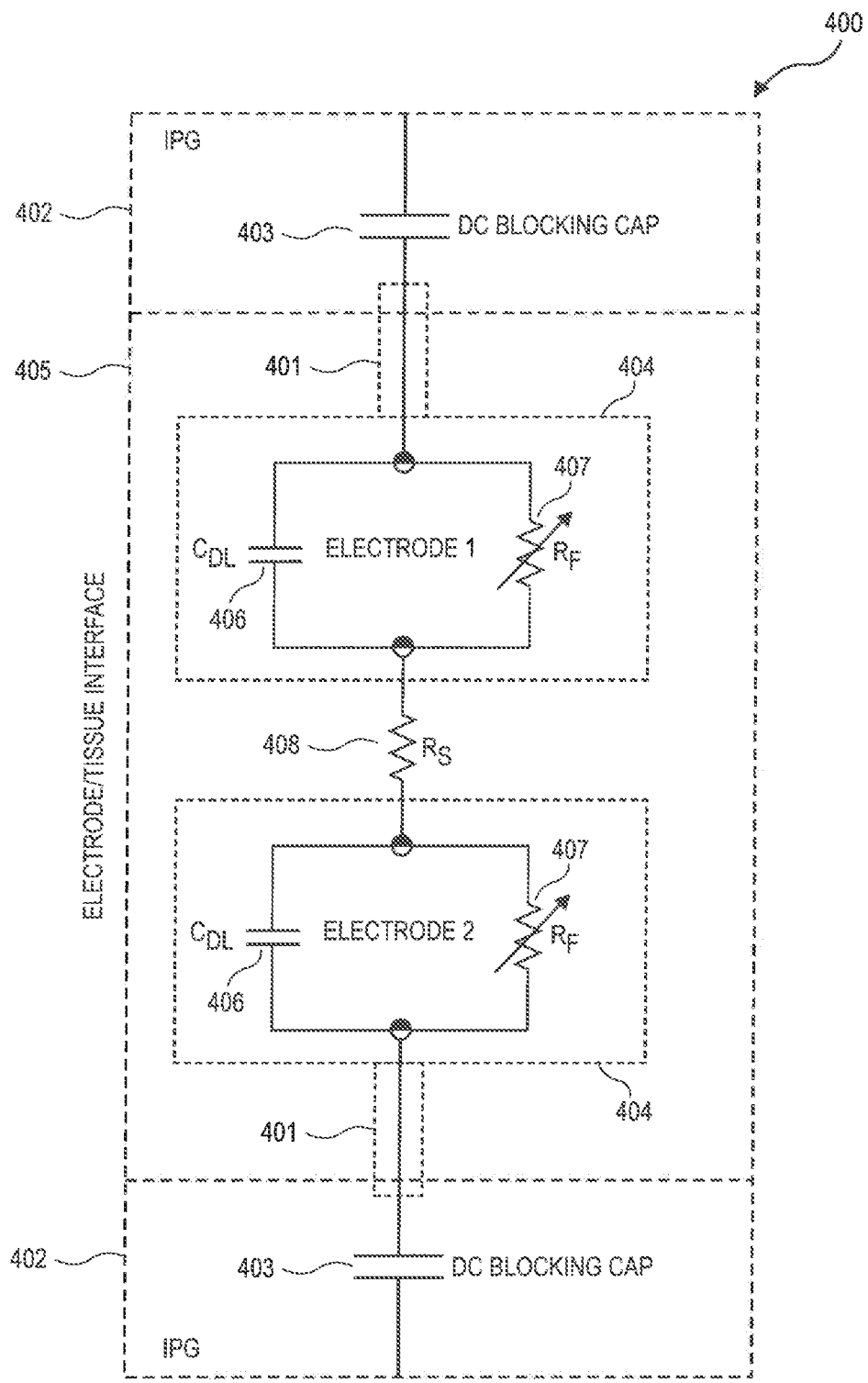
FIG. 4 depicts a model of the electrical interaction between a patient's tissue and stimulation electrodes.

FIG. 4 depicts a model 400 of the electrical interaction between a patient's tissue and stimulation electrodes. One or more stimulation leads 401 are connected to an IPG 402. The stimulation leads 401 are coupled to IPG 402 via DC blocking capacitors 403, which for safety reasons prevent DC current from being applied to the patient's tissue. As a component of IPG 402, the DC blocking capacitors 403 have a known value. In an example embodiment, DC blocking capacitors are 22 µF. Stimulation leads 401 comprise one or more electrodes 404, such as electrodes 132-135 (FIG. 1). When a stimulation therapy waveform is applied to a patient, one electrode 404 may be designated as an anode and the other electrode 404 is designated as a cathode such that charge flows from the anode electrode 404 to the cathode electrode 404. In an embodiment, one electrode may be the metallic case of IPG 402 that functions as an anode.

Model 400 depicts an electrode/tissue interface 405 that represents the electrical characteristics of the physical electrodes that reside in the patient's tissue. The electrode/tissue Interface 405 can be modeled as an RC network for each electrode comprising a parallel capacitor ($C_{DL}$) 406 in parallel with a variable resistance ($R_F$) 407, which are then in series with at least some portion of the patient tissue resistance ($R_S$) 408. Capacitor 406 represents the capacitive interface between the electrode and the tissue, which is a double layer (DL) capacitance. At the interface where the physical electrode 404 touches the patient's tissue, electrode 404 acts like a capacitor, which is represented by capacitor ($C_{DL}$) 406. Where the electrode 404 touches the patient's tissue there are also resistances, which is represented by Faradaic resistance ($R_F$) 407 and some portion of the patient tissue resistance ($R_S$) 408. Variable resistance 407 accounts for Faradaic conduction across the electrode/tissue interface that is dependent upon the stimulation current density. Resistance ($R_S$) 408 represents the resistance through and across the patient's tissue between electrodes 404, which is dependent upon the conductivity of the tissue and the effective surface areas of the electrodes. It will be understood that the specific values assigned to the resistances and capacitors in model 400 are dependent upon the type and deployment of electrodes in a particular patient and, therefore, model 400 is unique for each patient and stimulation lead.

The model 400 of an actual electrode/tissue interface 405 In a patient can be determined by taking voltage measurement samples, such as can be taken by IPG 402 across stimulation leads 401 and/or electrodes 404. If only a single voltage measurement is taken, then the electrode/tissue interface can be modelled only as a single resistance, which may or may not be adequate in assessing the impact of the electrodes upon the stimulation delivered by the IPG. However, this is an over-simplification of the load into which the IPG device delivers stimulation. IPG stimulation therapy is not instantaneous, but instead occurs over a period of time, Accordingly, model 400 represents a complex impedance load network for the IPG, which can take time-dependent effects into account, such as caused by capacitances in a load network. By determining model 400 for a patient, IPG 402 can monitor shifts in resistance and capacitance (e.g., $R_F$, $C_{DL}$, or $R_S$) over time during the life of the patient and device. This provides improved monitoring of lead integrity and patient health and position in some cases.

In an example embodiment, the following parameters may be used to model a directional DBS stimulation electrode:

Effective Electrode/Patient Interface Capacitance ($C_{DL}$)=0.1 µF;

Patient Load Resistance ($R_S$)=2KΩ; and

Residual Voltage after Stimulation ($V_{RESIDUAL}$)=3.6V (3 mA, 120 µS).

The Initial Discharge Amplitude ($I_{INITIAL}$) can be calculated as:

$$I_{INITIAL} = V_{RESIDUAL}/R_{LOAD} = 1.8 \text{ mA}$$

The Discharge Time Constant (T) can be calculated as:

$$T = R_S * C_{DL} = 0.2 \text{ mS}.$$

The emulated passive discharge current ($I_{DISCHARGE}$) at any time (t) is calculated as:

$$I_{DISCHARGE} = I_{INITIAL} * \exp(-t/T)$$

Table 1 is an example list of pre-calculated programmed discharge currents for one embodiment. Table 1 further includes a duration for each discharge current interval.

TABLE 1

| Time (µs) | Discharge Current Amplitude (mA) | Time Duration (µS) |
|---|---|---|
| 0 | 1.758 | 5 |
| 5 | 1.712 | 5 |
| 10 | 1.670 | 5 |
| ... | | |
| 500 | 0.141 | 10 |
| ... | | |
| 1000 (1 mS) | 0.0095 | 50 |

Figure 5:
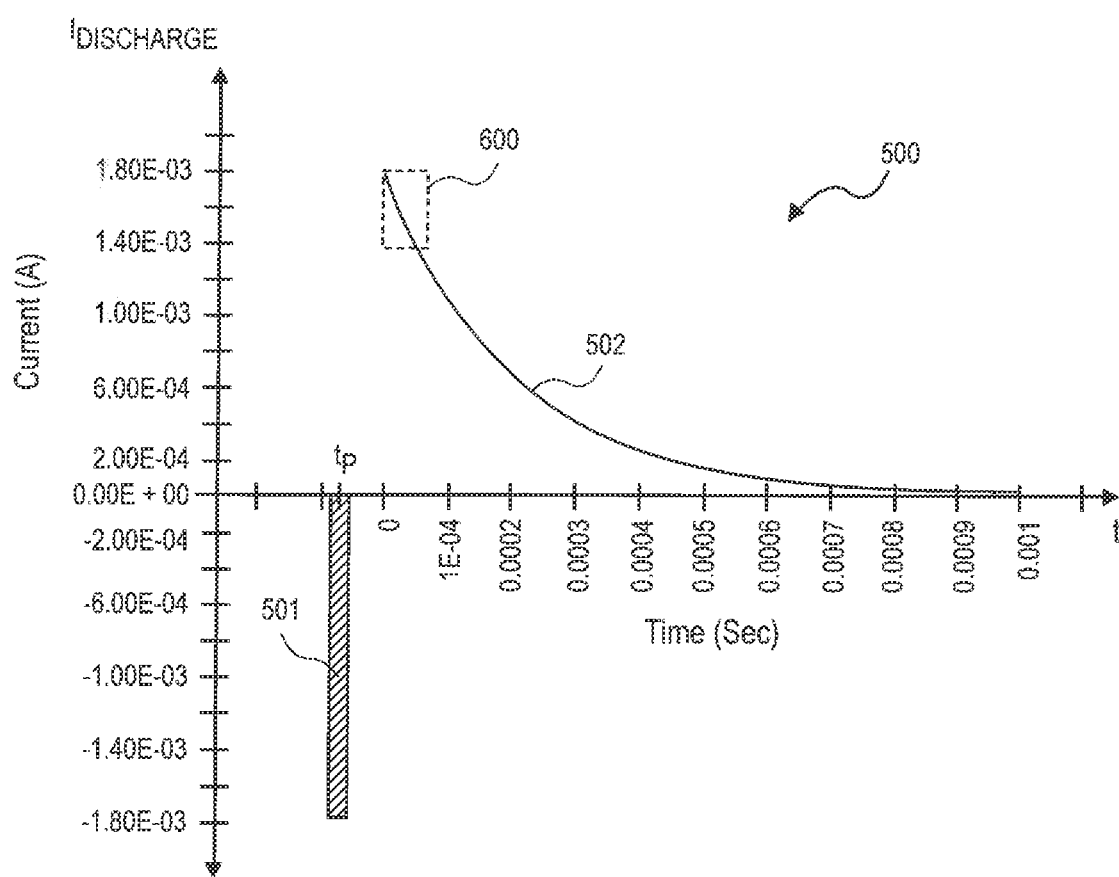
FIG. 5 depicts a plot of an emulated passive discharge current versus time according to one embodiment.

FIG. 5 depicts a plot 500 of an emulated passive discharge current ($I_{DISCHARGE}$) versus time (t) according to one embodiment illustrating the values shown in Table 1. At $t_P$ the IPG generates therapy pulse 501 that is applied to the patent via implanted electrodes. Then at time t=0, after the programmed therapy pulse width is over, the IPG enters the active discharge mode and reverses the electrodes so that anodes become cathodes and cathodes become anodes. During the active discharge mode, the exponentially-decreasing discharge current 502 applied to the electrodes is constantly changing according to pre-calculated values, such as illustrated in Table 1. Charge is essentially accumulated during the therapy pulse and then dissipated during active discharge, The therapy pulse will correspond to a programmed set of electrodes operating as anodes and cathodes. For active discharge, those same electrodes are used with the anode and cathode roles reversed.

Referring to the programmable amplitude current regulator 300 embodiment illustrated In FIG. 3, during active discharge the output of error amplifier 304 drives the gates of the cathode current sink NMOS transistors 306. The NMOS transistors 306 function as current sinks having a high output impedance, which causes the discharge circuit to appear as high impedance during an MRI. Error amplifier 304 has feedback so that it maintains high impedance during therapy stimulation and during the emulated passive discharge. This allows the current regulator 300 to maintain the stimulation loop as a high impedance the whole time that it is utilized, which avoids unintended current flow to be caused by the MRI magnetic field gradients.

However, since the active discharge phase requires battery power it may be preferred in some embodiments not use the active discharge circuit when not at risk of exposure to an MRI. Instead, an IPG in one embodiment may use the active discharge circuit only when directed by a clinician programmer device 202 (FIG. 2) or when the IPG detects an MRI environment (using magnetic field sensing circuitry as an example). In other embodiments, active discharge may be used more frequently or continuously if a patient is more likely to be exposed to EMI.

Figure 6:
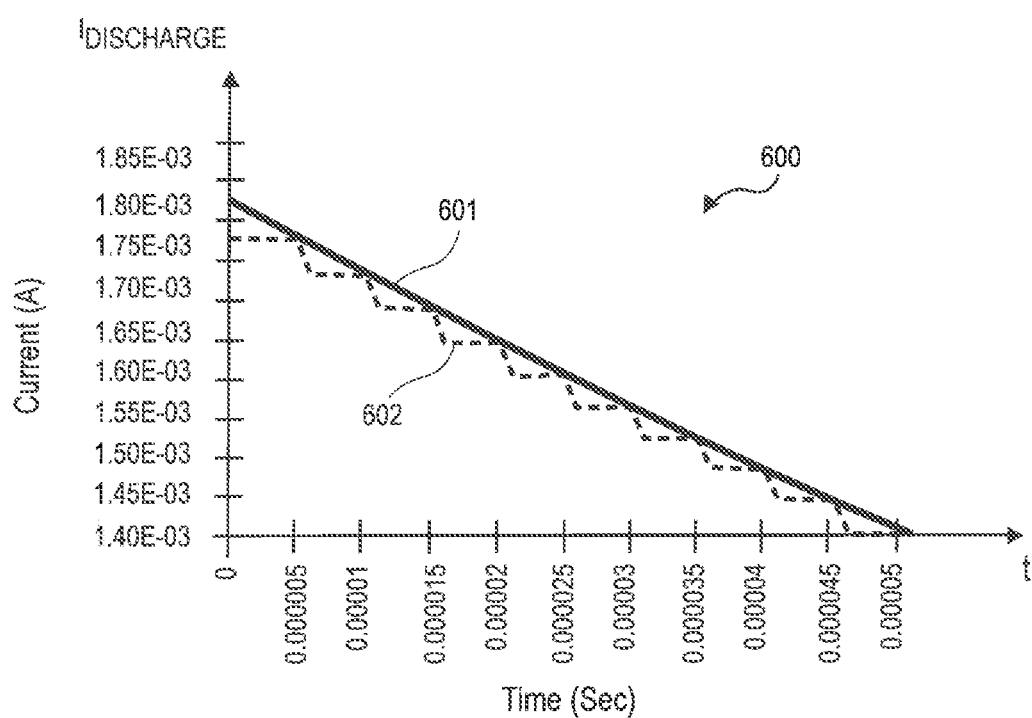
FIG. 6 depicts a zoomed-in view of region of the plot in FIG. 5 for an emulated passive discharge current according to one embodiment.

FIG. 6 depicts a zoomed-in view of region 600 of plot 500 (FIG. 5) for an emulated passive discharge current ($I_{DISCHARGE}$) versus time (t) according to one embodiment. Curve 601 represents the passive discharge current over time. Curve 602 represents the emulated passive discharge current created by an active discharge circuit. As illustrated in FIG. 6, the programmed current amplitude for the emulated passive discharge 602 has either the same current value as, or has a slightly lower value than, the current for passive discharge 601 at all times. This behavior ensures that the emulated passive discharge implementation does not unexpectedly recruit any neurons in non-target regions during electrode discharge after stimulation while closely mimicking the desired overall electrode discharge behavior normally attained by passive discharge.

The stimulation electrode discharge method in one embodiment utilizes a digitally programmable amplitude current regulator to electrically mimic passive discharge. Embodiments take advantage of knowledge of the IPG load impedance and residual charge on the load after stimulation to determine the current amplitude programming profile needed for discharge. This discharge method consists of using a calculated peak initial discharge current and exponential decay RC time constant. The load impedance characteristics may be measured using multiple impedance measures as discussed herein. Just as for passive discharge, the active discharge method exponentially decreases the discharge current via digitally programming changes in the current regulator discharge current amplitude at successive times to mimic the discharge current decrease during passive discharge after therapy stimulation. By controlling the discharge current amplitude's exponential decrease over time using a current regulator, the active discharge method avoids the creation of a low-impedance electrical loop between the IPG and the stimulation electrodes as would normally occur for passive discharge. By preventing the creation of a low-impedance electrical loop during the discharge phase after stimulation, the active discharge method prevents degradation in therapy and alleviates patient safety concerns, while maintaining patient therapy efficacy during an MRI scan or when exposed to other types of EMI.

Embodiments of the active discharge method are capable of closely mimicking passive discharge in a manner that minimizes the undesirable recruitment of neurons in proximity to the target region of the patient, as prior clinical trials have shown is avoided when using passive discharge. This may better prevent undesirable stimulation side effects compared to the delivery of a constant amplitude active discharge current, which is normally disallowed for use during DBS therapy.

Embodiments of the active discharge method use a programmable amplitude for a current regulator to mimic passive discharge, without creating a low-impedance electrical loop between the IPG and stimulation leads. Because a high-impedance loop must be maintained between the IPG and stimulation leads during an MRI scan or during other types of EMI, the use of a programmable, exponentially-decreasing amplitude for a current regulator for discharge after stimulation avoids degradation of the patient's therapy. This also mitigates safety concerns while continuously delivering stimulation to the patient during an MRI scan or EMI event Embodiments of the emulated passive discharge circuit provide the following and other advantages over other prior-art solutions for the discharge-during-MRI/EMI problem:
  alleviate the need for a doctor or clinician to create a custom DBStherapy program for use only during MRI/EMI, such as a custom "bipole" stimulation configuration as used in the prior-art,
  allow the IPG during MRI/EMI to automatically adjust the discharge method after stimulation to use an exponentially decaying discharge current regulator amplitude, which mimics passive discharge, while making use of the very same electrodes as were used for stimulation prior to the onset of the MRI scan or EMI event, such as, for example, monopolar stimulation,
  reduce the time burden on both the patient and doctors/clinicians during DBS IPG programming, since there is no need to program special stimulation configurations for handling MRI/EMI conditions, and
  minimize the possibility of DBS therapy side effects caused during constant-current discharge after stimulation, since constant-current discharge conditions may cause the unintended recruitment of non-target neurons which could result in undesirable therapeutic side effects.

The emulated passive discharge method after stimulation is not as battery-current efficient as the use of passive discharge. However, MRI scans and EMI events are of relatively short duration (e.g., typically, 30 minutes to 2 hours) and occur sporadically for a patient in addition, the battery-current efficiency degradation resulting from the active novel discharge method may not be substantial compared to use of prior-art "bipole" configurations for maintaining stimulation therapy during MRI/EMI events. Typical "bipole" stimulation configurations are usually not as efficient as monopolar stimulation configurations, The emulated passive discharge method is compatible with either monopolar or bipolar stimulation configurations. Accordingly, there are numerous advantages from the use of the emulated passive discharge method, including: therapy efficacy, reduced side effects, reduced programming burden, and improved patient safety, in addition to the benefit of maintaining patient therapy delivery during MRI/EMI events.

Figure 7:
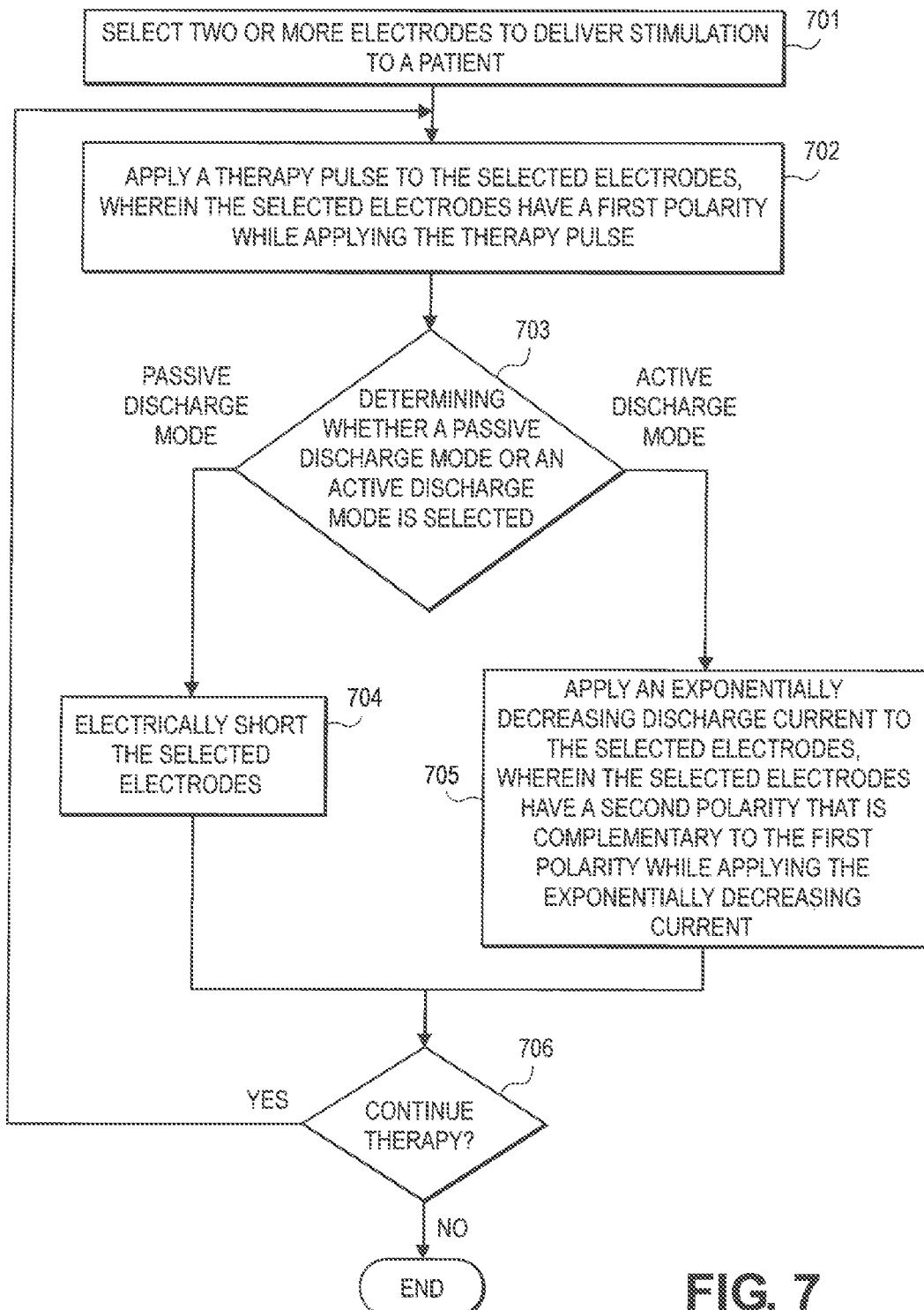
FIG. 7 depicts a flowchart illustrating a method for discharging electrodes in an implantable medical device.

FIG. 7 depicts a flowchart illustrating a method for discharging electrodes in an implantable medical device (IMD). In step 701, one or more electrodes are selected to deliver stimulation to a patient using the IMD. In step 702, a therapy pulse is applied from the IMD to the selected electrodes. The selected electrodes have a first polarity while applying the therapy pulse. In an embodiment, the selected electrodes function as anodes and cathodes in the first polarity. In step 703, a determination is made whether the IMD is operating in a passive discharge mode or an active discharge mode. In one embodiment, the IMD is in communication with an external programming device and receives an active discharge mode command from the external programming device. In another embodiment, the IMD comprises circuitry for identifying the presence of MRI activity or EMI, such as circuitry for detecting electrical and/or magnetic fields. Upon such detection, the IMD may enter an emulated passive discharge mode.

If the IMD Is operating in a passive discharge mode, then in step 704, the selected electrodes are electrically shorted to dissipate stored charge. If the IMD is operating in an active discharge mode, then in step 705, an exponentially decreasing current is applied from the IMD to the selected electrodes having a second polarity which is opposite the first polarity. In an embodiment, the selected electrodes function in a complementary fashion as cathodes and anodes In the second polarity.

In step 706, after completing the passive or exponentially decreasing active discharge in steps 704 or 705, the device determines if therapy should continue. If therapy has been completed, then the process ends. If therapy should continue, then the process returns to step 702 to provide additional therapy pulses.

In one embodiment, the exponentially decreasing discharge current is applied using a programmable current source comprising an error amplifier having a first input coupled to a programmable voltage source and a second input coupled to a programmable resistor. A current at an output of the current regulator is determined by a voltage of the programmable voltage source and a resistance of the programmable resistor. The current output of the current regulator may be decreased in precalculated steps to create the exponentially decreasing discharge current applied to the electrodes.

Figure 9:
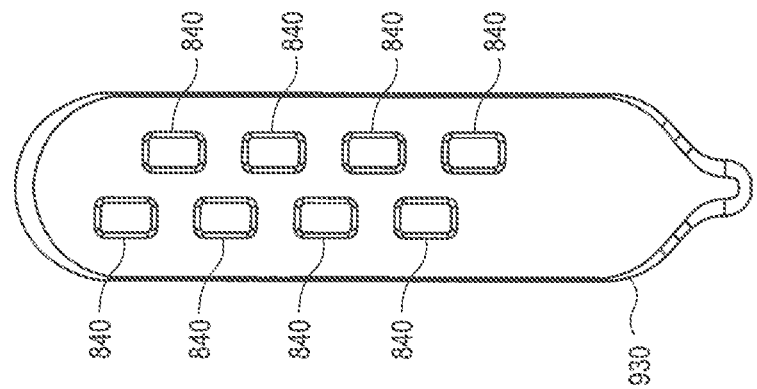
FIG. 9 depicts a paddle lead stimulation portion for inclusion at the distal end of a stimulation lead according to example embodiments.
Figure 8B:
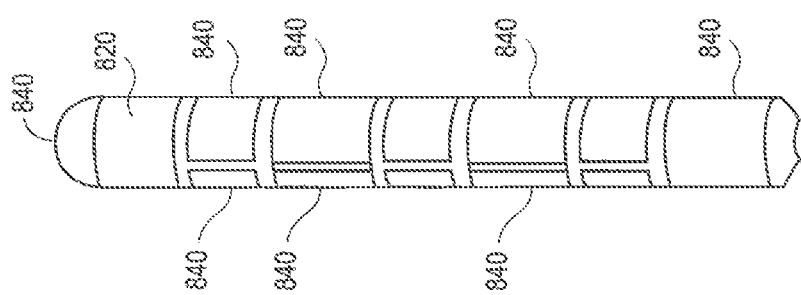
FIGS. 8A and 8B respectively depict stimulation portions for inclusion at the distal end of a stimulation lead according to example embodiments.
Figure 8A:
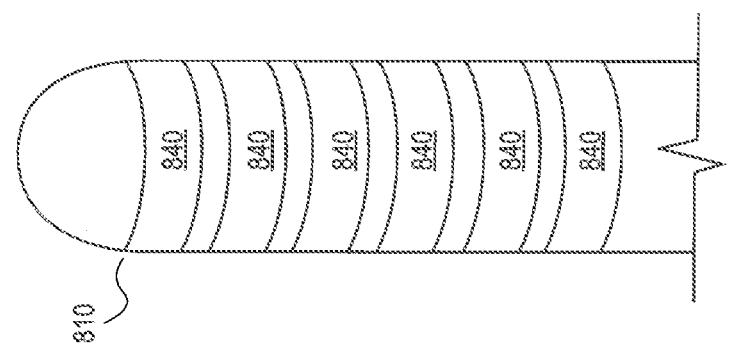

FIGS. 8A-8B respectively depict stimulation portions 810, 820 for inclusion at tile distal end of a stimulation lead 130 according to example embodiments. FIG. 9 depicts paddle lead stimulation portion 930 according to example embodiments. Stimulation portions 810, 820, and 930 each include one or more electrodes 840. Stimulation portion 810 depicts a conventional stimulation portion of a "percutaneous" lead with multiple ring electrodes. Stimulation portion 820 depicts a stimulation portion including several "segmented electrodes." The term "segmented electrode" is distinguishable from the term "ring electrode." As used herein, the term "segmented electrode" refers to an electrode of a group of electrodes that are positioned at the same longitudinal location along the longitudinal axis of a lead and that are angularly positioned about the longitudinal axis so they do not overlap and are electrically isolated from one another. Example fabrication processes are disclosed in U.S. Pat. No. 9,054,436, entitled, "METHOD OF FABRICATING STIMULATION LEAD FOR APPLYING ELECTRICAL STIMULATION TO TISSUE OF A PATIENT," which is incorporated herein by reference. Stimulation portion 930 includes multiple planar electrodes on a paddle structure.

Embodiments are directed to a method for using voltage waveformcapture of a current-controlled therapeutic stimulation waveform to provide modelling of a complex impedance for the electrode/tissue interface. Instead of requiring external test equipment, this measurement capability may be included in an implantable device, which allows for long-term patient monitoring and more realistic modelling of tissue load. Most accepted electrode/tissue interface models are represented by a complex impedance network having capacitors and variable resistors in addition to simple resistances, so multiple samples over time become necessary to accurately determine the load model for the stimulation device.

Figure 10:
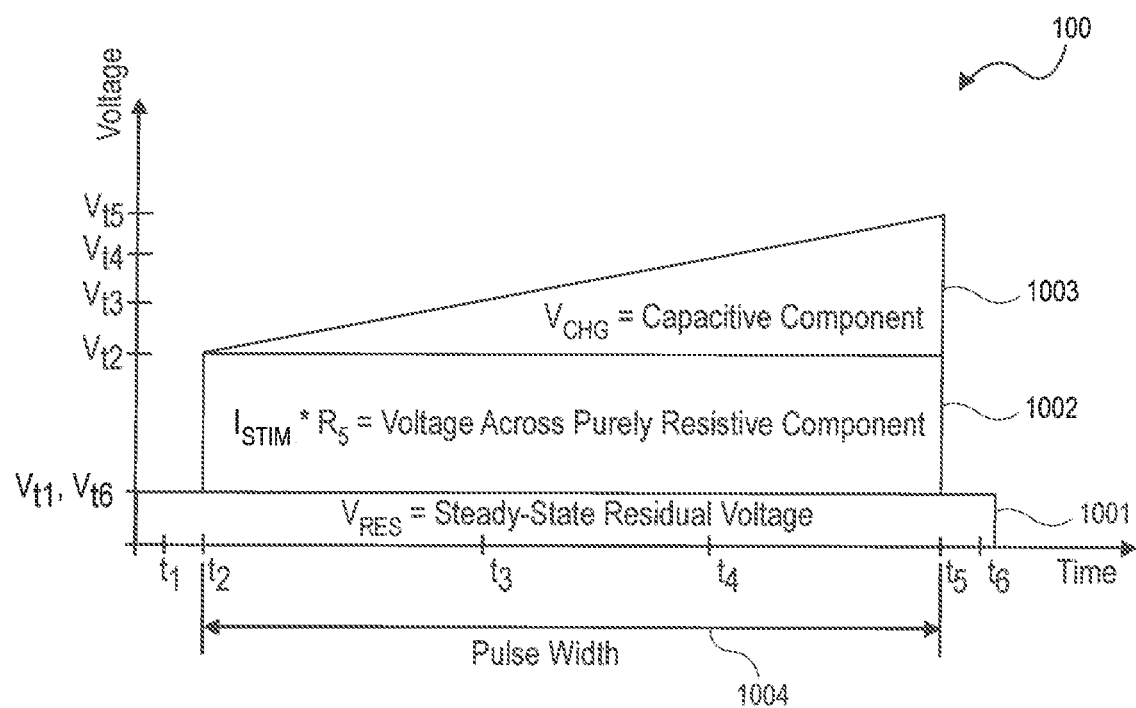
FIG. 10 is a plot illustrating components of a voltage load across the model shown in FIG. 4 as a result of a constant-current therapy pulse.

FIG. 10 is a plot 1000 illustrating the components of the voltage across load model 400 (FIG. 4) resulting from a constant-current therapy pulse. Voltage component 1001 is the steady-state residual voltage ($V_{RES}$) that is present on stimulation leads 401 and/or electrodes 404. This voltage may correspond to the undischarged voltage that has built up during prior therapy pulses and, therefore, may exist before and after the therapy pulse is generated. Voltage component 1002 corresponds to the voltage created by the stimulation current ($I_{STIM}$) across the resistive component $R_S$ 408 of the electrode/tissue interface. Component 1003 corresponds to the voltage ($V_{CHG}$) added by charge on capacitors $C_{DL}$ 406, which increases throughout the duration 1004 of the therapy pulse. Knowledge of the double-layer capacitance value is a critical input to understanding the electrode/tissue interface. It is known that both the double-layer capacitance $C_{DL}$ 406 and the Faradaic conduction $R_F$ 407 vary with stimulation current density. As a result, it is important to be able to take complex impedance measurements using the delivered therapeutic stimulation pulse.

Figure 11:
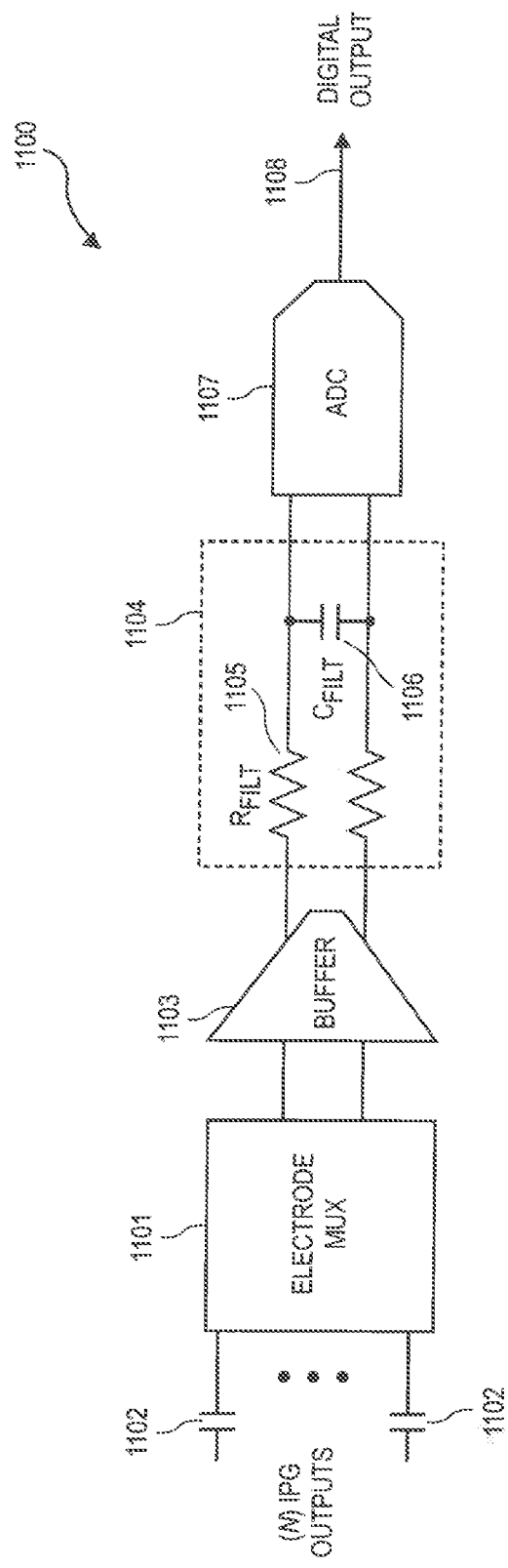
FIG. 11 depicts a circuit that can be used for the complex impedance measurements of an electrode/tissue interface.

FIG. 11 depicts a circuit 1100 that can be used for the complex impedance measurements of an electrode/tissue interface. Electrode multiplexer (MUX) 1101 is coupled to a plurality (N) IPG electrode leads (not shown). Electrode MUX 1101 may be connected to the electrodes through stimulation or sensing DC blocking capacitors 1102. Electrode MUX 1101 selects sets of the IPG electrode leads to be evaluated and sends signals from those leads to buffer 1103. Differential buffer 1103 attenuates the voltage signal of the load so that measurements can be made using therapeutic stimulation waveforms. Electrode MUX 1101 selects sets of the IPG electrode leads to be evaluated and sends buffered voltage signals from those leads to Filter circuit 1104, comprising the two resistances RFILT 1105 and CFILT 1106, isolates analog-to-digital converter (ADC) 1107 and prevents aliasing. The differential ADC 1107 digitizes signals of either positive or negative polarity and outputs digital data 1108. Circuit 1100 captures entire stimulation response voltage waveforms from the electrode leads. Alternatively, circuit 1100, may capture strategic measurement points on each load response waveform at multiple times for simpler post-processing calculations in generating the complex impedance model of the electrode/tissue interface. The captured waveforms and/or measurement points on each waveform represented by output 508 may be stored in memory for additional processing to evaluate the waveform components.

Referring to FIG. 10, for example, circuit 1100 may be used to capture voltages for a stimulation therapy pulse at different time points $t_1$ through $t_6$, which occur before, during, and after the stimulation therapy is applied. The voltage measured at time points $t_1$ and $t_6$ occur outside the delivery of therapy. Accordingly, the voltages ($V_{RES}$) at these intervals are associated with residual voltage on the electrodes. Once identified, this voltage can be subtracted from measurements captured during the stimulation therapy. The voltages measured at time points $t_2$ and $t_5$ occur at the beginning and end of the stimulation therapy, respectively. The stimulation therapy is typically applied at a constant current $I_{STIM}$ for a certain time duration or pulse width. Using this known current and the measured voltage at the start of the therapy pulse (i.e., at time $t_2$), the value of the patient's tissue resistance ($R_S$ 408, FIG. 4) can be calculated using Ohm's law (e.g., $R_S = V_{t2} - V_{t1}/I_{STIM}$).

As the current from the stimulation therapy is applied to the electrodes, charge builds up on the double layer capacitor ($C_{DL}$ 406, FIG. 4) in the electrode/tissue interface model. The value of the double layer capacitor can be determined by measuring the change in voltage as charge is delivered (i.e., $C = Q/\Delta V$ where C is the value of the capacitor, Q is the charge on the capacitor, and $\Delta V$ is change in voltage across the capacitor). The value of $\Delta V$ can be determined from the slope of segment 1003 in FIG. 10, such as the difference between $V_{t2}$ and $V_{t5}$ when a constant-current stimulation therapy pulse starts and stops or from the difference between other voltages during the therapy pulse, such as between $V_{t3}$ and $V_{t1}$. The amount of charge Q can be estimated from the integration of the therapy current $I_{STIM}$ over the pulse width 1004 duration. Using these values, the double layer capacitor ($C_{DL}$) value can be estimated. The value of the Faradaic resistance (R=407, FIG. 4) in the electrode/tissue interface model may be estimated by nonlinearities in the measured voltage versus time, based upon the estimated $C_{DL}$ capacitance and stimulation current density, for example.

The electrode/tissue interface may be modeled continuously (i.e., for each therapy pulse) or intermittently (e.g., at predetermined intervals, or upon the occurrence of events, such as changes in the therapy schedule). Models of the electrode/tissue interface may be calculated for each set of anode/cathode electrodes that are used to provide therapy and/or that are implanted in the patient. These models may be compared over time (and/or at various stimulation current densities) to evaluate the operation of the electrodes, leads, and/or IPG and to detect changes in the device and/or the patient's health. As discussed herein, the IPG may modify its emulated passive discharge according to a most recent electrode/tissue model calculated from the measurements.

Figure 12:
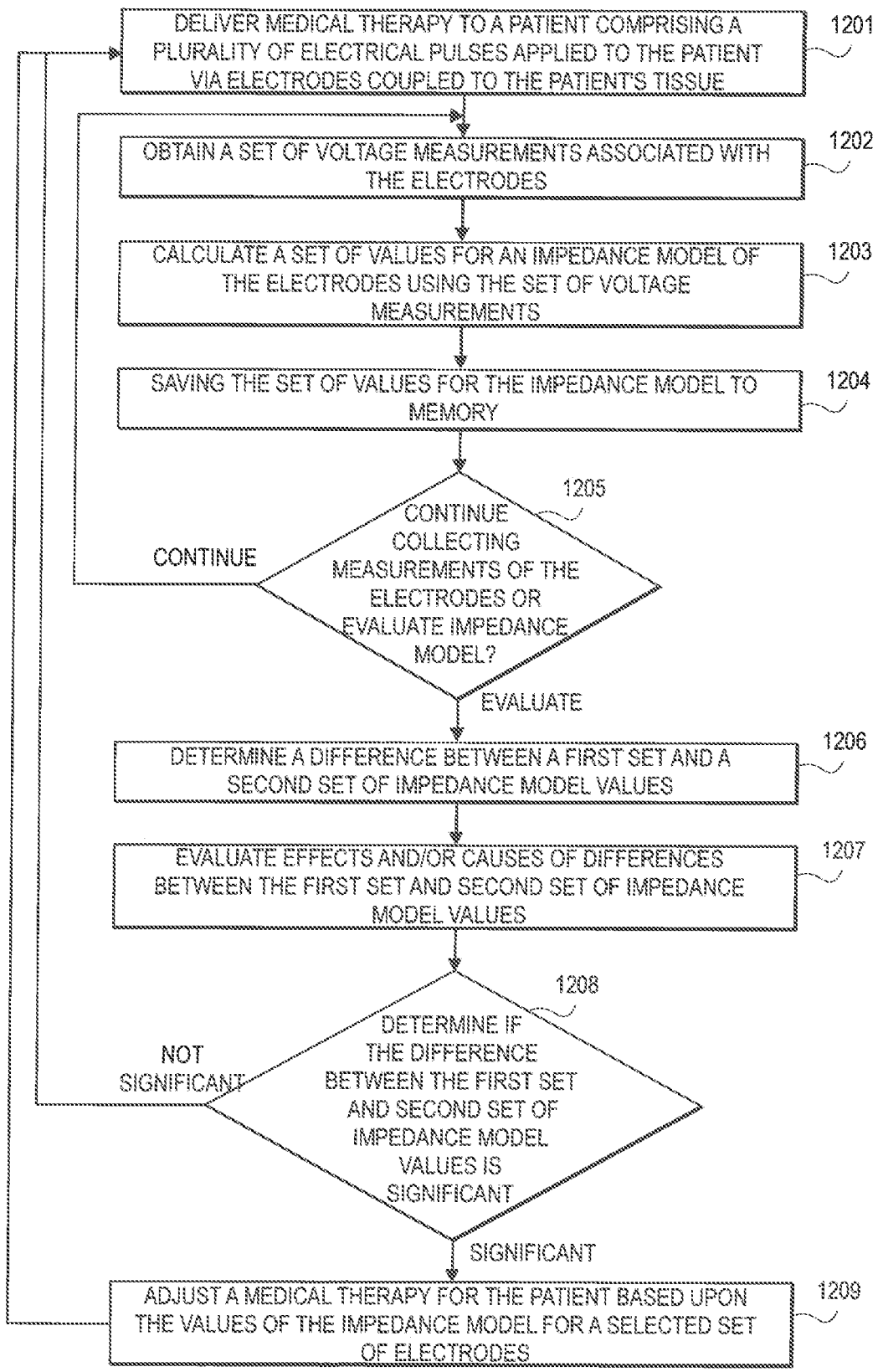
FIG. 12 depicts a flowchart illustrating a method for monitoring electrodes in an implantable medical device (IMD).

FIG. 12 depicts a flowchart illustrating a method for monitoring electrodes in an implantable medical device. In step 1201, stimulation therapy is delivered to a patient. The stimulation therapy comprises a plurality of electrical waveforms applied to the patient via electrodes coupled to the patient's tissue. Instep 1202, a set of voltage measurements associated with the electrodes are obtained. In step 1203, a set of values for an impedance model of the electrodes is calculated using the set of voltage measurements. In step 1204, the set of values for the impedance model are saved to memory. In step 1205, the process evaluates whether additional measurements of the electrodes should be collected and/or if the impedance model should be evaluated. If additional measurements are desired, then the process returns to step 1202 and additional voltage measurements are collected for other therapy waveforms and additional sets of impedance model values are calculated and stored.

In addition to collecting additional measurements, the process may evaluate the previously collected sets of impedance model values. In step 1206, a difference between a first set of impedance model values and a second set of impedance model values is determined. For example, the difference may be determined to correspond to a change in status for the set of electrodes, such as failure of the electrodes, movement of the electrodes, excessive charge build-up on the electrodes, and the like. Alternatively, the difference may be determined to correspond to a change in the health of the patient. In step 1207, the process evaluates the effects and/or causes of the difference between the first and second sets of impedance model values. In step 1208, a determination is made as to whether or not the difference between the two sets of impedance models is significant. The amount of difference between the impedance model values that is considered to be significant may be established as a minimum amount or a percentage difference, for example, that is based upon the type of therapy being delivered and/or the type or model of implanted device. If the difference is not significant then the process returns to step 1201 to monitor additional therapy Waveforms. If the difference is significant, then the process moves to step 1209, where a stimulation therapy for the patient is adjusted based upon the values for the impedance model for a selected set of electrodes. In various embodiments, this adjustment may comprise adjusting a therapy pulse amplitude, duration, and/or frequency or selecting different electrode(s) to deliver the therapy pulse. In some embodiments, the IPG may modify its emulated passive discharge according to the most recent electrode/tissue model calculated from the measurements.

One or more of the operations described above in connection with the methods may be performed using one or more processors. The different devices in the systems described herein may represent one or more processors, and two or more of these devices may include at least one of the same processors. In one embodiment, the operations described herein may represent actions performed when one or more processors (e.g., of the devices described herein) execute program instructions stored in memory (for example, software stored on a tangible and non-transitory computer readable storage medium, such as a computer hard drive, ROM, RAM, or the like).

The processor(s) may execute a set of instructions that are elements may also store data or other information as desired or needed. The storage element may be in the form of an information source or a physical memory element within the controllers and the controller device. The set of instructions may include various commands that instruct the controllers and the controller device to perform specific operations such as the methods and processes of the various embodiments of the subject matter described herein. The set of instructions may be in the form of a software program. The software may be in various forms such as system software or application software. Further, the software may be in the form of a collection of separate programs or modules, a program module within a larger program or a portion of a program module. The software also may include modular programming in the form of object-oriented programming. The processing of input data by the processing machine may be in response to user commands, or in response to results of previous processing, or in response to a request made by another processing machine.

The controller may include any processor-based or microprocessor-based system including systems using microcontrollers, reduced instruction set computers (RISC), application specific integrated circuits (ASICs), field-programmable gate arrays (FPGAs), logic circuits, and any other circuit or processor capable of executing the functions described herein. When processor-based, the controller executes program instructions stored in memory to perform the corresponding operations. Additionally, or alternatively, the controllers and the controller device may represent circuits that may be implemented as hardware. The above examples are exemplary only and are thus not intended to limit in any way the definition and/or meaning of the term "controller".

It is to be understood that the subject matter described herein is not limited in its application to the details of construction and the arrangement of components set forth in the description herein or illustrated in the drawings hereof. The subject matter described herein is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the invention without departing from its scope. While the dimensions, types of materials and coatings described herein are intended to define the parameters of the invention, they are by no means limiting and are exemplary embodiments. Many other embodiments will be apparent to those of skill in the art upon reviewing the above description. The scope of the invention should, therefore, be determined with reference to the appended claims, along with the full scope of equivalents to which such claims are entitled. In the appended claims, the terms "including" and "in which" are used as the plain—English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f), unless and until such claim limitations expressly use the phrase "means for" followed by a statement of function void of further structure.

The invention claimed is:

1. An implantable pulse generator (IPG) for providing a neurostimulation therapy, comprising:
   therapeutic stimulation circuitry for controlling generation and delivery of electrical pulses to a patient using one or more electrodes of a stimulation lead;
   measurement circuitry for determining characteristics of the one or more electrodes;
   a processor for controlling the IPG according to executable code; and
   memory for storing data and the executable code, wherein the executable code comprises instructions for causing the processor to:
   determine a plurality of voltage measurements for the one or more selected electrodes during delivery of a respective pulse of the neurostimulation therapy applied to the patient; and
   manage an emulated passive discharge based on the determined plurality of voltage measurements.

2. The IPG of claim 1, wherein the executable code further comprises instructions for causing the processor to adjust a medical therapy for the patient based upon the determined plurality of voltage measurements for the one or more electrodes.

3. The IPG of claim 1, wherein the executable code further comprises instructions for causing the processor to save a first set of values for an impedance model for the one or more selected electrodes, save a second set of values for the impedance model for the one or more selected electrodes, and identify a difference between the first set of values and the second set of values.

4. The IPG of claim 3, wherein the difference corresponds to a change in at least one of the health of the patient or status of the one or more selected electrodes.

5. The IPG of claim 1, further comprising an active discharge circuit, wherein the executable code comprises instructions for causing the processor to cause the active discharge circuit to create the emulated passive discharge.

6. The IPG of claim 5, further comprising a digitally programmable amplitude current regulator coupled to the active discharge circuit, wherein the executable code comprises instructions for causing the processor to modify the amplitude current regulator to modify the emulated passive discharge.

7. The IPG of claim 1, wherein the emulated passive discharge is modified by changing a programmed current amplitude for the emulated passive discharge to have either a same current value as, or has a slightly lower value than, a current for a passive discharge.

8. The IPG of claim 1, wherein the executable code further comprises instructions for causing the processor to calculate a set of values for an impedance model of the one or more electrodes using the determined plurality of voltage measurements, wherein the impedance model comprises a capacitance associated with an electrode/tissue interface and a resistance associated with tissue between electrodes.

9. The IPG of claim 8, wherein the capacitance associated with the electrode/tissue interface corresponds to a rate of change of voltage measurements captured during a stimulation therapy waveform.

10. The IPG of claim 8, wherein the resistance associated with tissue between electrodes corresponds to a voltage measurement captured at the beginning of a therapy waveform.

11. A method of controlling a neurostimulation therapy using an implantable pulse generator (IPG) comprising:
    delivering a neurostimulation therapy to a patient using one or more electrodes of a stimulation lead, the neurostimulation therapy comprising a plurality of electrical pulses generated by the IPG;
    obtaining a first set of voltage measurements for the one or more electrodes during delivery of a respective pulse of the neurostimulation therapy applied to the patient; and
    modifying an emulated passive discharge based on the first set of voltage measurements.

12. The method of claim 11, further comprising:
    adjusting one or more stimulation parameters for a neurostimulation therapy for the patient based upon the values for the first set of voltage measurements for a selected set of electrodes.

13. The method of claim 11, further comprising:
    calculating a first set of values for an impedance model of the one or more electrodes using the first set of voltage measurements;
    obtaining a second set of voltage measurements associated with the one or more electrodes;
    calculating a second set of values for an impedance model of the electrodes using the second set of voltage measurements; and
    determining a difference between the first set of values and the second set of values.

14. The method of claim 13, wherein the difference corresponds to a change in status for a set of electrodes.

15. The method of claim 13, wherein the difference corresponds to a change in the health of the patient.

16. The method of claim 13, wherein the impedance model comprises a capacitance associated with an electrode/tissue interface and a resistance associated with tissue between electrodes.

17. The method of claim 11, wherein a capacitance associated with an electrode/tissue interface corresponds to a rate of change of voltage measurements captured during a therapy waveform.

18. The method of claim 11, wherein a resistance associated with tissue between electrodes corresponds to a voltage measurement captured at the beginning of a therapy waveform.

19. The method of claim 11, further comprising causing an active discharge circuit to create the emulated passive discharge.

20. The method of claim 11, wherein the emulated passive discharge is modified by changing a programmed current amplitude for the emulated passive discharge to have either a same current value as, or has a slightly lower value than, a current for a passive discharge.

* * * * *